US010883136B2

(12) United States Patent
Kwon et al.

(10) Patent No.: US 10,883,136 B2
(45) Date of Patent: Jan. 5, 2021

(54) METHOD OF ISOLATING BIOCHEMICAL MOLECULES ON MICROARRAY SUBSTRATE

(71) Applicant: SNU R&DB FOUNDATION, Seoul (KR)

(72) Inventors: Sunghoon Kwon, Seoul (KR); Taehoon Ryu, Gyeonggi-do (KR); Yeongjae Choi, Seoul (KR); Yushin Jung, Seoul (KR); Hyoki Kim, Seoul (KR); Howon Lee, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 83 days.

(21) Appl. No.: 14/650,311

(22) PCT Filed: Dec. 9, 2013

(86) PCT No.: PCT/KR2013/011362
§ 371 (c)(1),
(2) Date: Jun. 7, 2015

(87) PCT Pub. No.: WO2014/088380
PCT Pub. Date: Jun. 12, 2014

(65) Prior Publication Data
US 2015/0322485 A1    Nov. 12, 2015

(30) Foreign Application Priority Data

Dec. 7, 2012    (KR) .................. 10-2012-0142009

(51) Int. Cl.
| *C12Q 1/6806* | (2018.01) |
| *G01N 33/50* | (2006.01) |
| *C12Q 1/24* | (2006.01) |
| *B01J 19/00* | (2006.01) |

(52) U.S. Cl.
CPC ............ *C12Q 1/6806* (2013.01); *B01J 19/00* (2013.01); *B01J 19/0046* (2013.01); *C12Q 1/24* (2013.01); *G01N 33/50* (2013.01); *B01J 2219/0054* (2013.01); *B01J 2219/00441* (2013.01); *B01J 2219/00452* (2013.01); *B01J 2219/00531* (2013.01); *B01J 2219/00608* (2013.01); *B01J 2219/00659* (2013.01); *B01J 2219/00689* (2013.01); *B01J 2219/00711* (2013.01); *B01J 2219/00716* (2013.01); *B01J 2219/00722* (2013.01); *B01J 2219/00725* (2013.01)

(58) Field of Classification Search
None
See application file for complete search history.

(56) References Cited

U.S. PATENT DOCUMENTS

| 6,093,302 | A | 7/2000 | Montgomery | |
| 2002/0120127 | A1* | 8/2002 | Church ............... | C12Q 1/6837 536/25.3 |
| 2004/0096907 | A1* | 5/2004 | Bohrmann ......... | G01N 33/6827 435/7.1 |
| 2004/0113606 | A1 | 6/2004 | Hayashizaki | |
| 2005/0018036 | A1 | 1/2005 | Barron | |
| 2006/0121500 | A1* | 6/2006 | Bachman ............. | B01L 3/5027 435/6.11 |
| 2007/0281310 | A1 | 12/2007 | Hoh | |
| 2012/0079894 | A1 | 4/2012 | Van Berkel et al. | |
| 2014/0155297 | A1* | 6/2014 | Heinz ................ | C12N 15/1093 506/30 |
| 2015/0072873 | A1* | 3/2015 | Heinz ................ | C12N 15/1065 506/4 |

FOREIGN PATENT DOCUMENTS

| CN | 1678738 A | 10/2005 |
| CN | 101035910 A | 9/2007 |
| CN | 102037351 A | 4/2011 |
| CN | 102292635 A | 12/2011 |
| WO | WO02066550 A1 | 8/2002 |
| WO | WO2003039750 A1 | 5/2003 |
| WO | WO03054543 A2 | 7/2003 |
| WO | WO03056320 A2 | 7/2003 |
| WO | WO2005107949 A1 | 11/2005 |
| WO | WO2006041938 A2 | 4/2006 |

OTHER PUBLICATIONS

International Search Report for PCT/KR2013/011362 dated Mar. 20, 2014 from Korean Intellectual Property Office.
Hu et al., Detection of multiple proteins on one spot by laser ablation inductively coupled plasma mass spectrometry and application to immuno-microarray, with element-tagged antibodies, Analytical Chemistry., 2007, vol. 79, No. 3. pp. 923-929.
S. Thalhammer et al., Laser Microtools in Cell Biology and Molecular Medicine, Laser Physics, vol. 13, No. 5, 2003, pp. 681-691.
Mark Schena et al., Quantitative Monitoring of Gene Expression Patterns with a Complementary DNA Microarray, Science, vol. 270, Oct. 20, 1995.
A. P. Blanchard et al., High-density oligonucleotide arrays, Biosensors & Bioelectronics, vol. 11, No. 6/7, pp. 687-690, 1996.
Stephen P. A. Fodor et al., Light-Directed Spatially Addressable Parallel Chemical Synthesis, Science, vol. 251,Feb. 15, 1991.

(Continued)

*Primary Examiner* — Christopher M Gross
(74) *Attorney, Agent, or Firm* — STIP Law Group, LLC

(57) ABSTRACT

Provided is a method of isolating biochemical molecules on a microarray substrate, the method including providing a microarray substrate to which clusters of different kinds of biochemical molecules being classified by individual spot units are attached, the individual spots being regularly arranged thereon; obtaining location information of the individual spot in which a desired cluster among clusters of the biochemical molecules locates; locating an extraction tool for applying energy to isolate the desired cluster according to the location information; and isolating the desired cluster from the microarray substrate by applying energy in a contact or non-contact manner using the extraction tool.

16 Claims, 12 Drawing Sheets

(56) References Cited

OTHER PUBLICATIONS

Hwangbeom Kim et al., Shotgun DNA synthesis' for the high-throughput construction of large DNA molecules, Nucleic Acids Research, 2012, vol. 40. No. 18.
Wood et al., Single cell trapping and DNA damage analysis using microwell arrays, PNAS Early Edition, pp. 1-6.
Jingdong Tian et al., Accurate multiplex gene synthesis from programmable DNA microchips, Nature, vol. 432, 23/30, Dec. 2004.
Daniel G Gibson et al., Enzymatic assembly of DNA molecules up to several hundred kilobases, Nature Methods, vol. 6, No. 5, May 2009.
William J. Blake et al., Pairwise selection assembly for sequence-independent construction of long-length DNA, Nucleic Acids Research, 2010, vol. 38, No. 8, pp. 2594-2602.
Haohao Lin et al., Replication of DNA Microarrays from Zip Code Masters, J. Am. Chem. Soc. 2006, 128, 3268-3272.
Sriram Kosuri et al., Scalable gene synthesis by selective amplification of DNA pools from high-fidelity microchips; nature biotechnology vol. 28 No. 12 Dec. 2010.
A. Karaiskou et al.; Microfabrication of biomaterials by the sub-ps laser-induced forward transfer process; Applied Surface Science; vol. 208-209, 2003; pp. 245-249; Elsevier Science; Netherland.
A. Zergioti et al.; Time resolved schlieren study of sub-pecosecond and nanosecond laser transfer of biomaterials; Applied Surface Science; vol. 247; 2005; pp. 584-589; Elsevier Science; Netherland.
Office Action form European Patent Office of 13 860 108.3, dated Oct. 28, 2020.

\* cited by examiner

[Fig. 1]
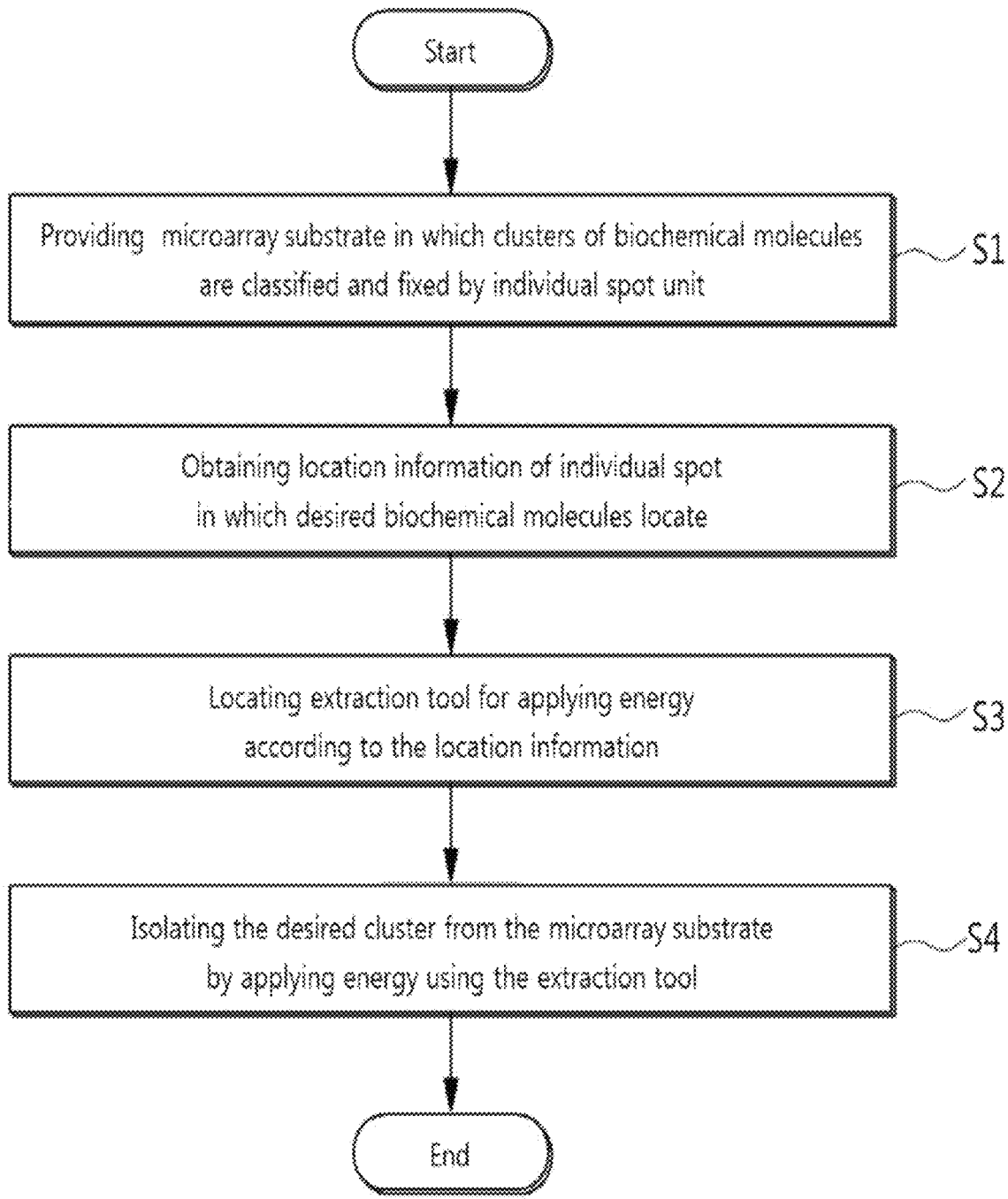

[Fig. 2]
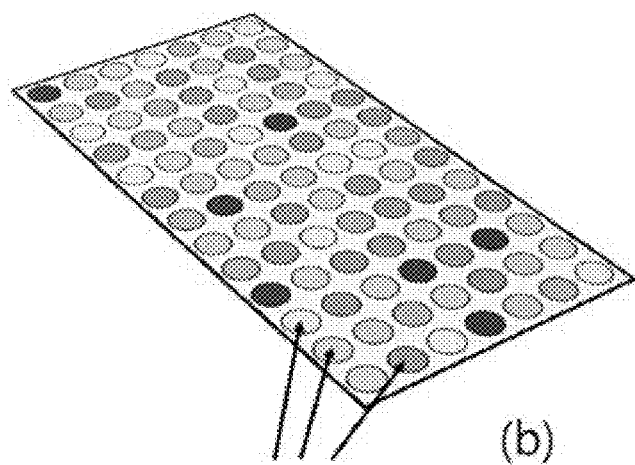
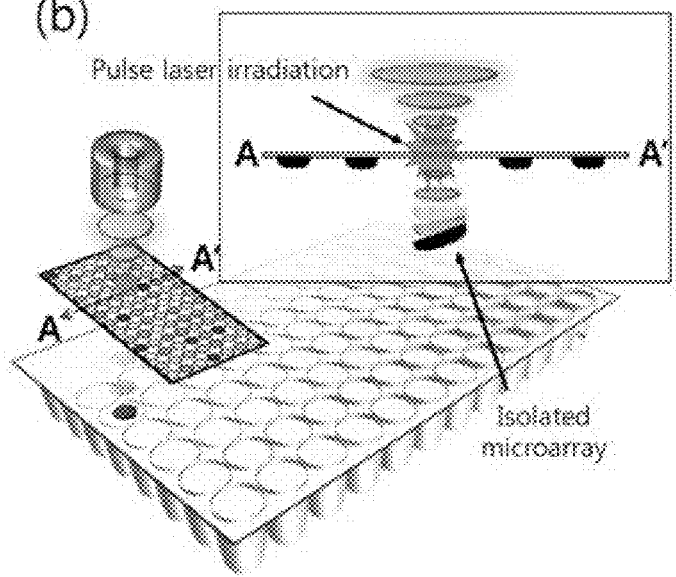
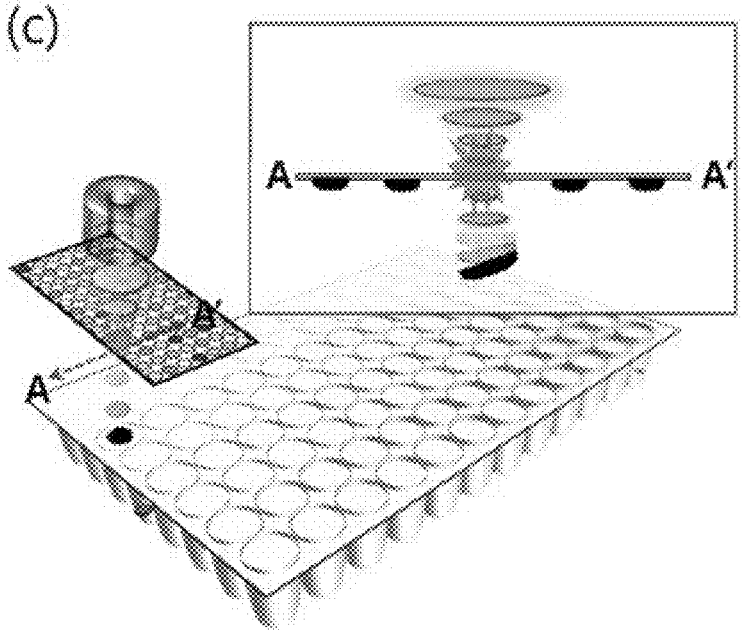

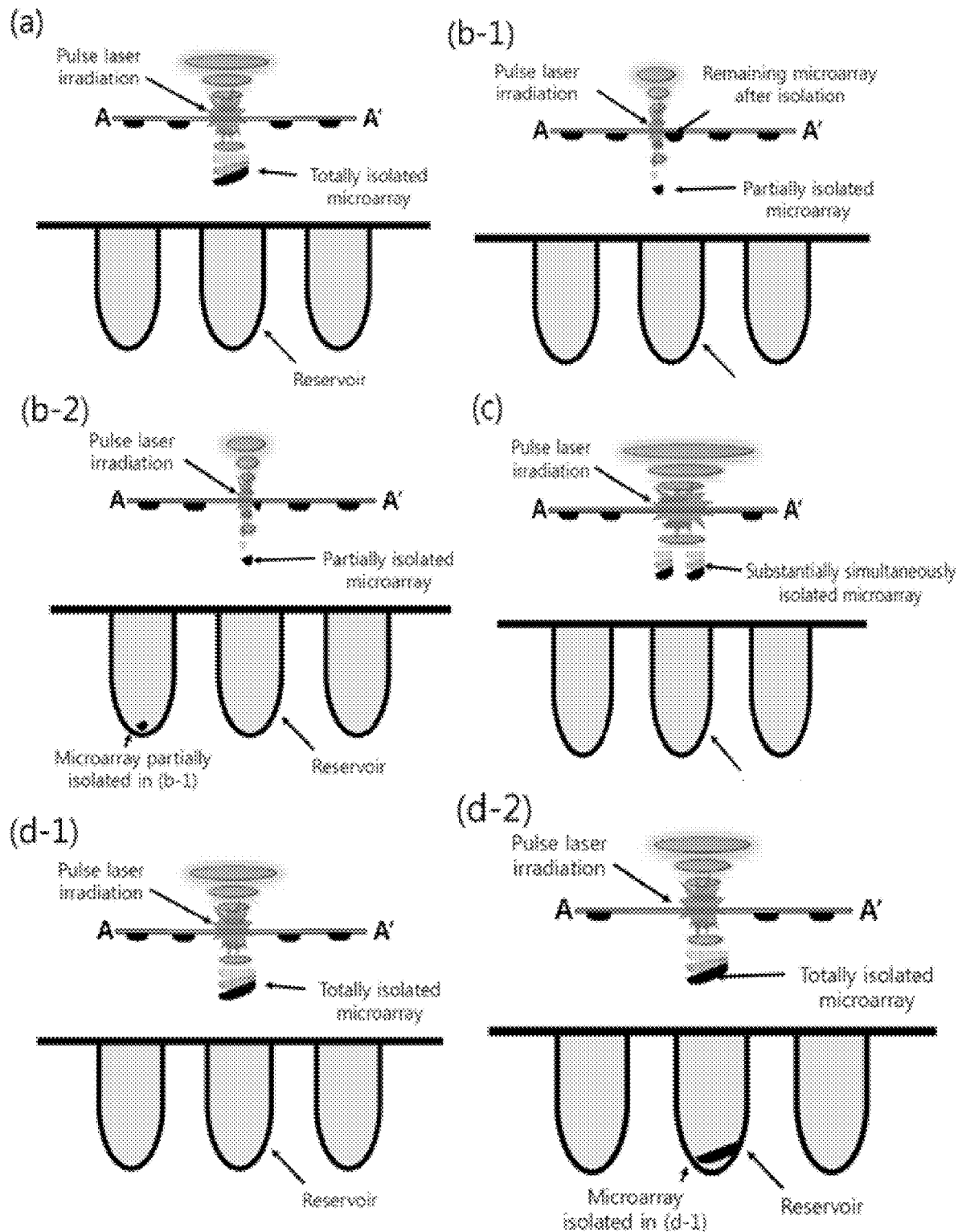
[Fig. 3]

[Fig. 4]
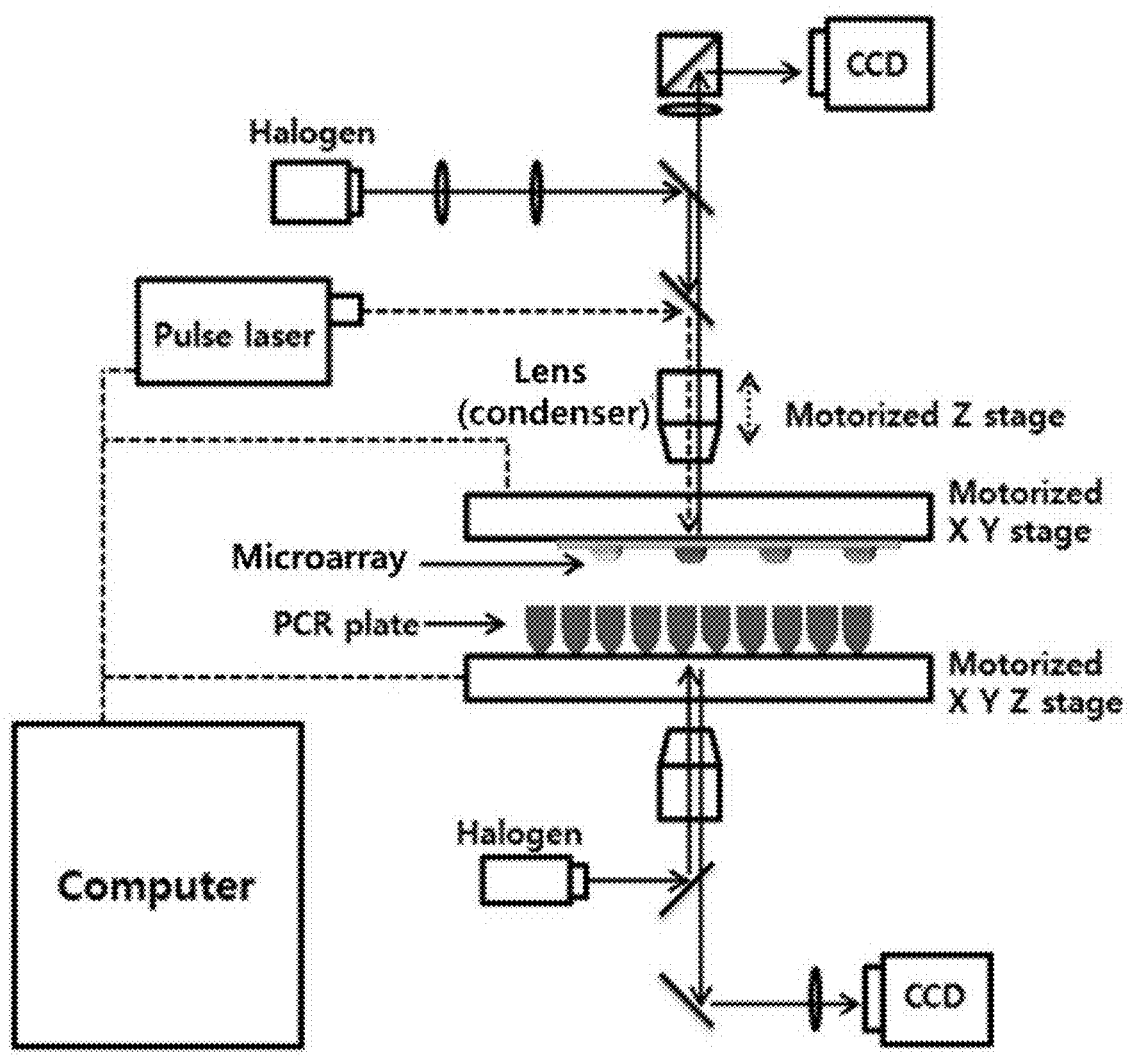

[Fig. 5]
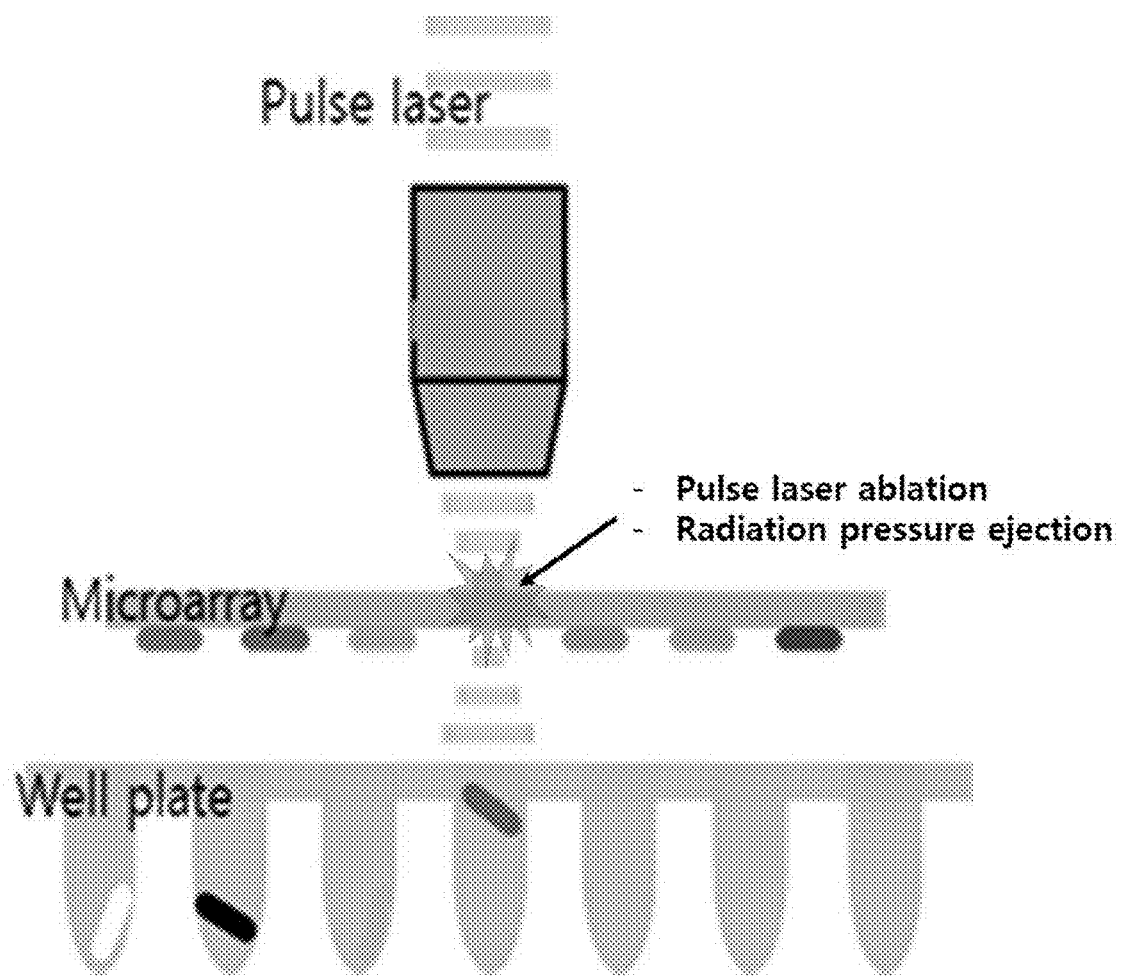

[Fig. 6]
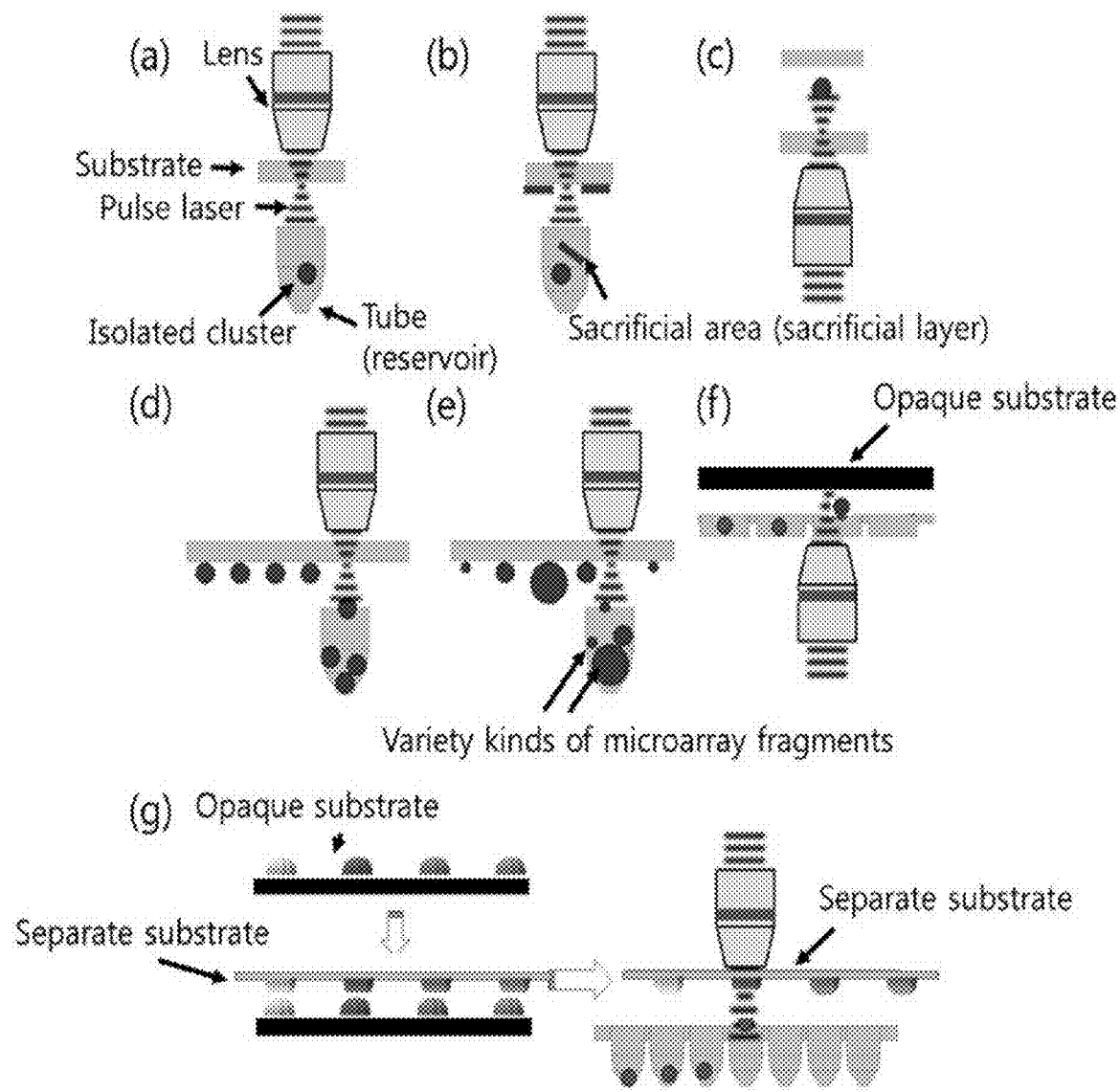

[Fig. 7]

| ID | Sequence |
|---|---|
| 1 | TGCGTGTCTCCGACTCAGTTATGACGTTATTCCGCCAGTGTGCTGGAATT |
| 2 | TGCGTGTCTCCGACTCAGTACTTTGATTGTGCCGCCAGTGTGCTGGAATT |
| 3 | TGCGTGTCTCCGACTCAGGAGACAATGCTACCCGCCAGTGTGCTGGAATT |
| 4 | TGCGTGTCTCCGACTCAGTTACCGGTCGGAACCGCCAGTGTGCTGGAATT |
| 5 | TGCGTGTCTCCGACTCAGTCGATCGGTTGAACCGCCAGTGTGCTGGAATT |
| 6 | TGCGTGTCTCCGACTCAGTCTATCACGCCTGGCGCCAGTGTGCTGGAATT |
| 7 | TGCGTGTCTCCGACTCAGTCTTCGAAGTTAGCCGCCAGTGTGCTGGAATT |
| 8 | TGCGTGTCTCCGACTCAGACATCGAGCGGGCACGCCAGTGTGCTGGAATT |
| 9 | TGCGTGTCTCCGACTCAGATATGTACATATTTCGCCAGTGTGCTGGAATT |
| 10 | TGCGTGTCTCCGACTCAGACCTCTACAATGGACGCCAGTGTGCTGGAATT |
| 11 | TGCGTGTCTCCGACTCAGTGCGCAAAACATTCGCCAGTGTGCTGGAATT |
| 12 | TGCGTGTCTCCGACTCAGCCCTCATCACAATTCGCCAGTGTGCTGGAATT |
| 13 | TGCGTGTCTCCGACTCAGGAACTAAAGGGCGCCGCCAGTGTGCTGGAATT |
| 14 | TGCGTGTCTCCGACTCAGGAGACGTATTCCCCGCCAGTGTGCTGGAATT |
| 15 | TGCGTGTCTCCGACTCAGGGTTGCTGCTTGGGCGCCAGTGTGCTGGAATT |
| 16 | TGCGTGTCTCCGACTCAGACCATAAAACCTCACGCCAGTGTGCTGGAATT |
| 17 | TGCGTGTCTCCGACTCAGTTCACCGCGGAACCCGCCAGTGTGCTGGAATT |
| 18 | TGCGTGTCTCCGACTCAGCGACTATGCGACTGCGCCAGTGTGCTGGAATT |
| 19 | TGCGTGTCTCCGACTCAGGACGGCCTATTTACCGCCAGTGTGCTGGAATT |
| 20 | TGCGTGTCTCCGACTCAGCGAGAGCTGTTCGACGCCAGTGTGCTGGAATT |
| 21 | TGCGTGTCTCCGACTCAGAGGCTGGTTGAATACGCCAGTGTGCTGGAATT |
| 22 | TGCGTGTCTCCGACTCAGCATGGCAGAAGATTCGCCAGTGTGCTGGAATT |
| 23 | TGCGTGTCTCCGACTCAGGAGGTGTCCTAAACCGCCAGTGTGCTGGAATT |
| 24 | TGCGTGTCTCCGACTCAGTTACGCGGCCATAACGCCAGTGTGCTGGAATT |

[Fig. 8]
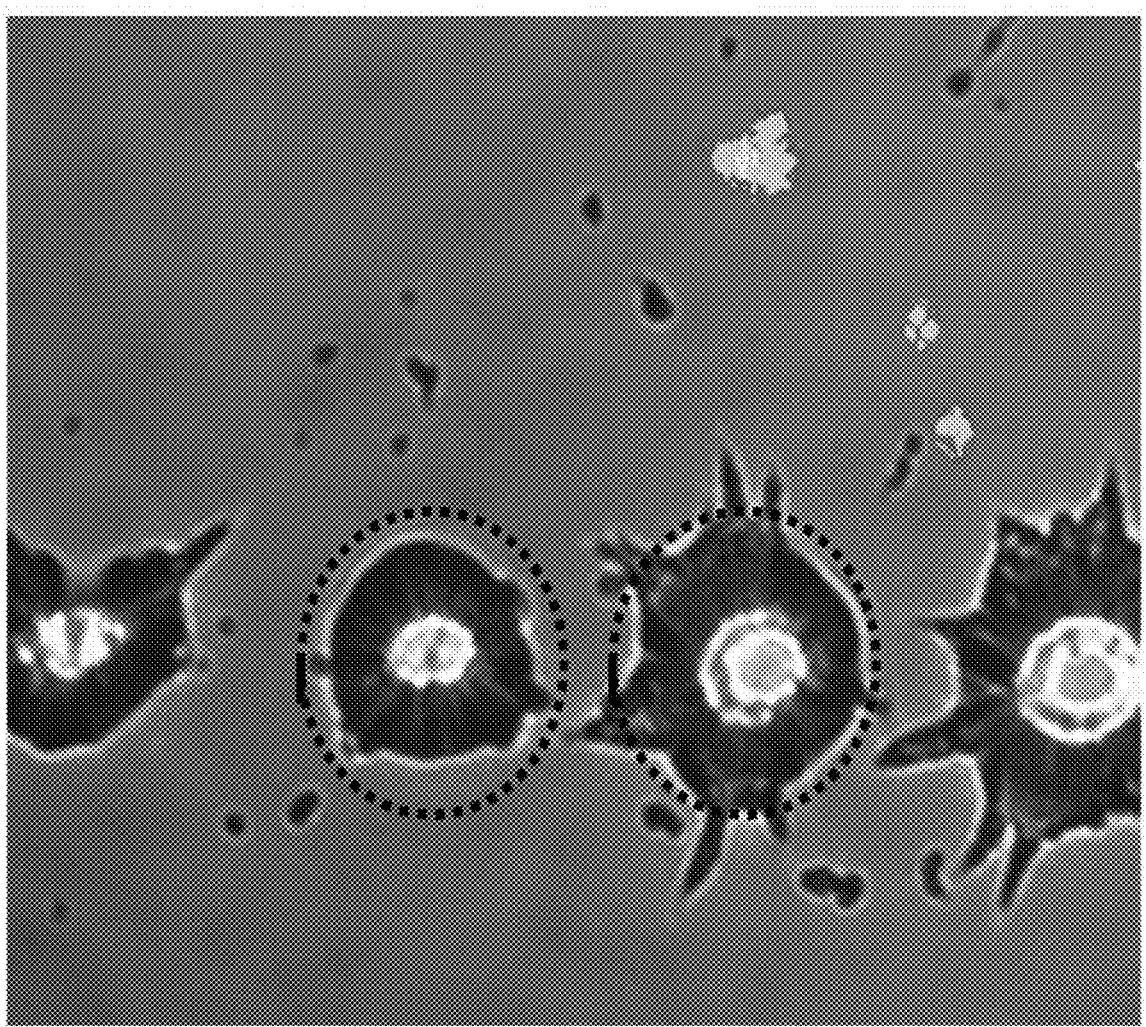

[Fig. 9]
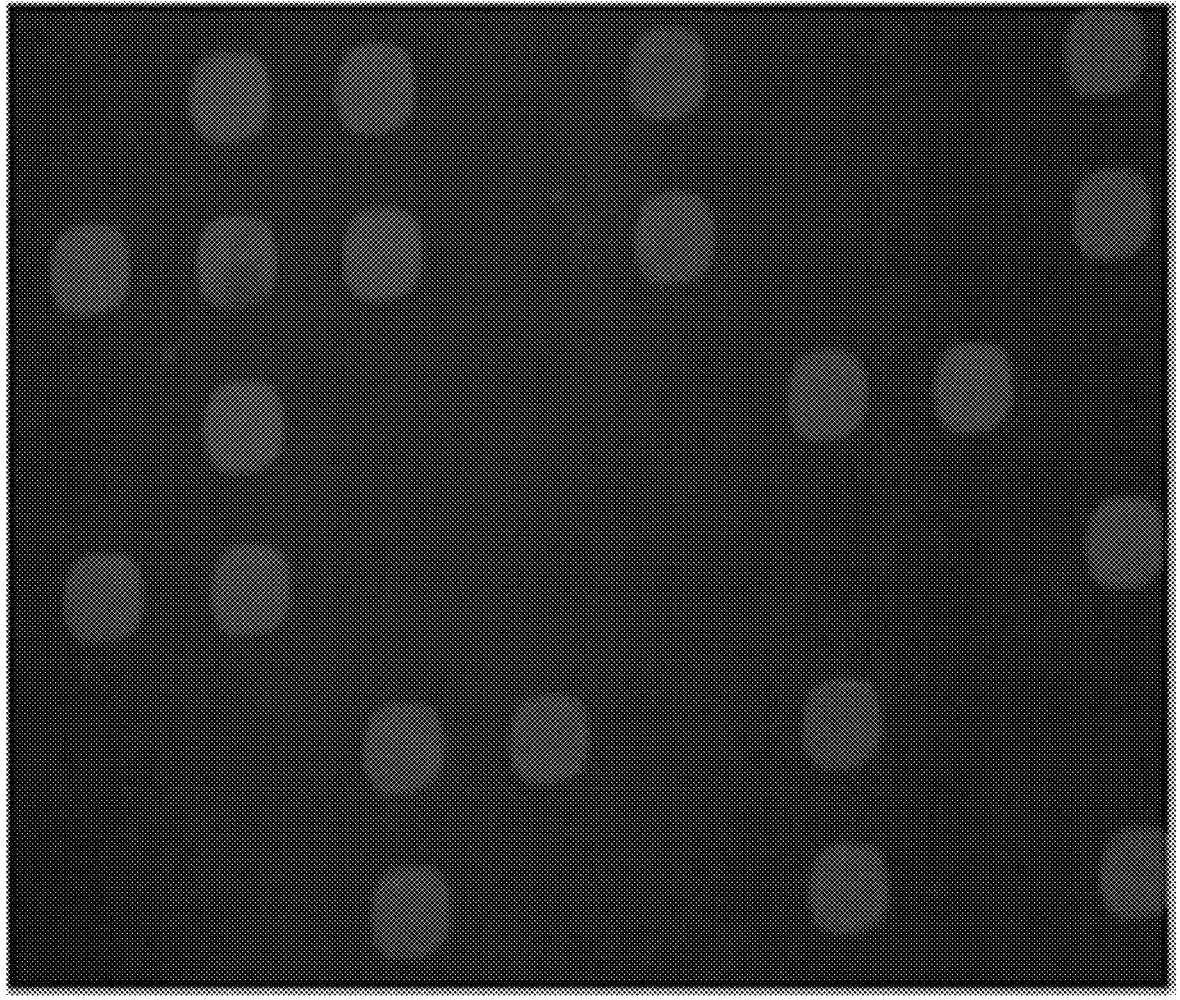

[Fig. 10]
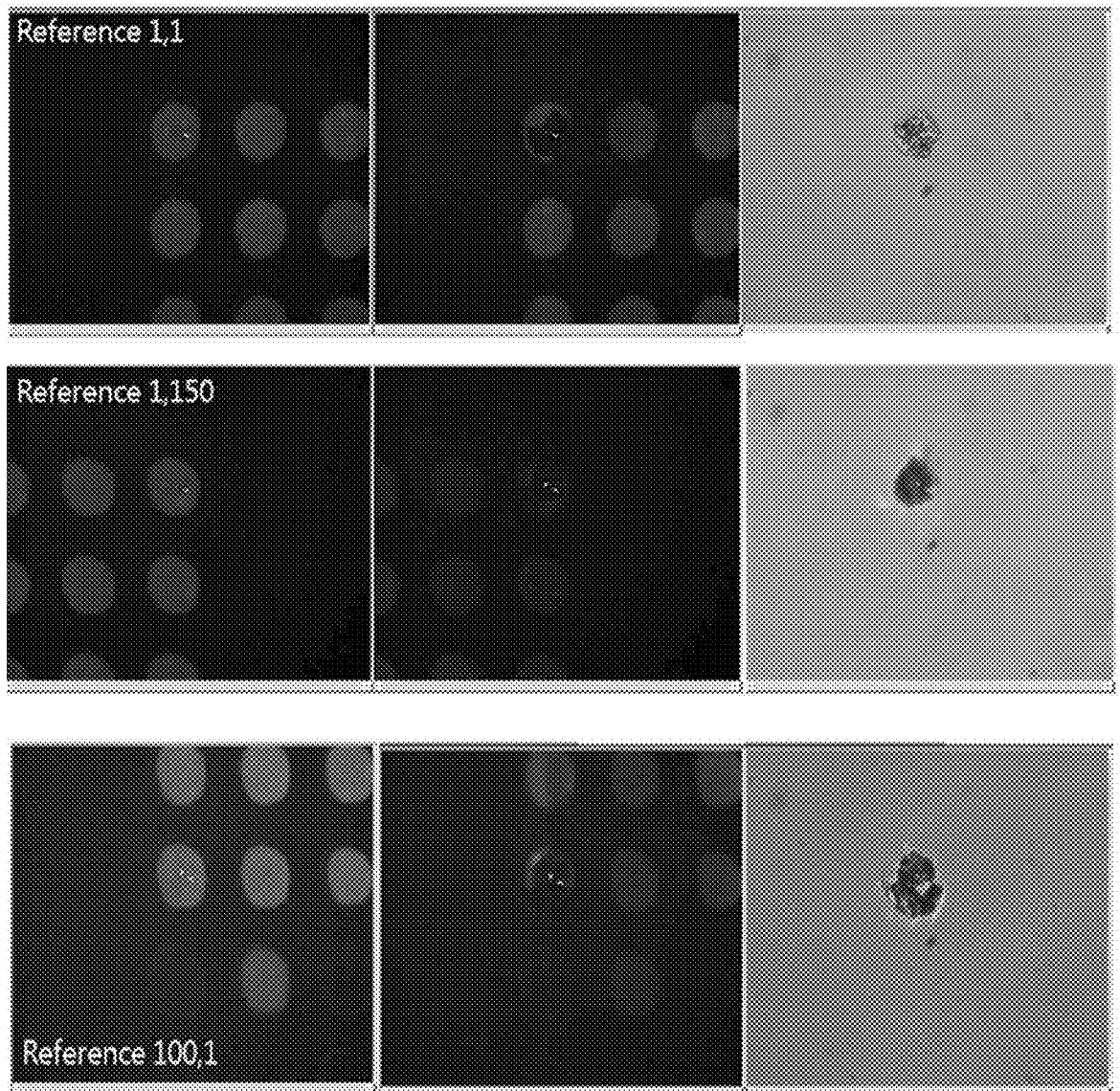

[Fig. 11]
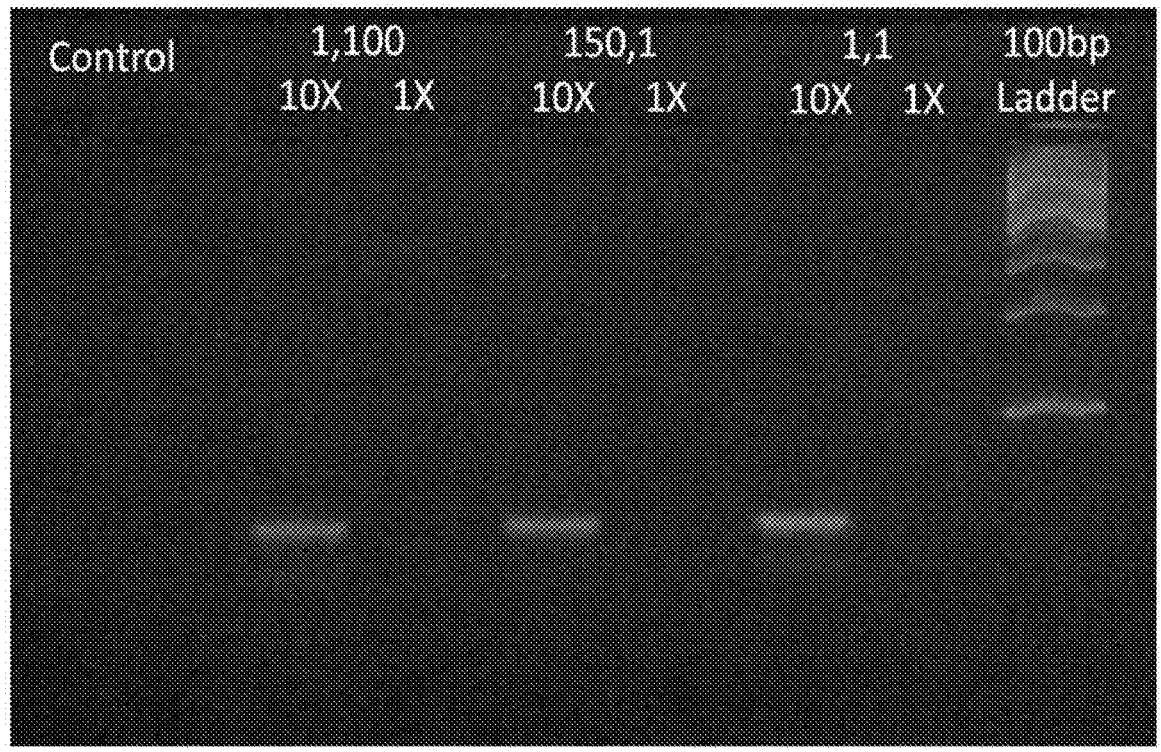
[Fig. 12]
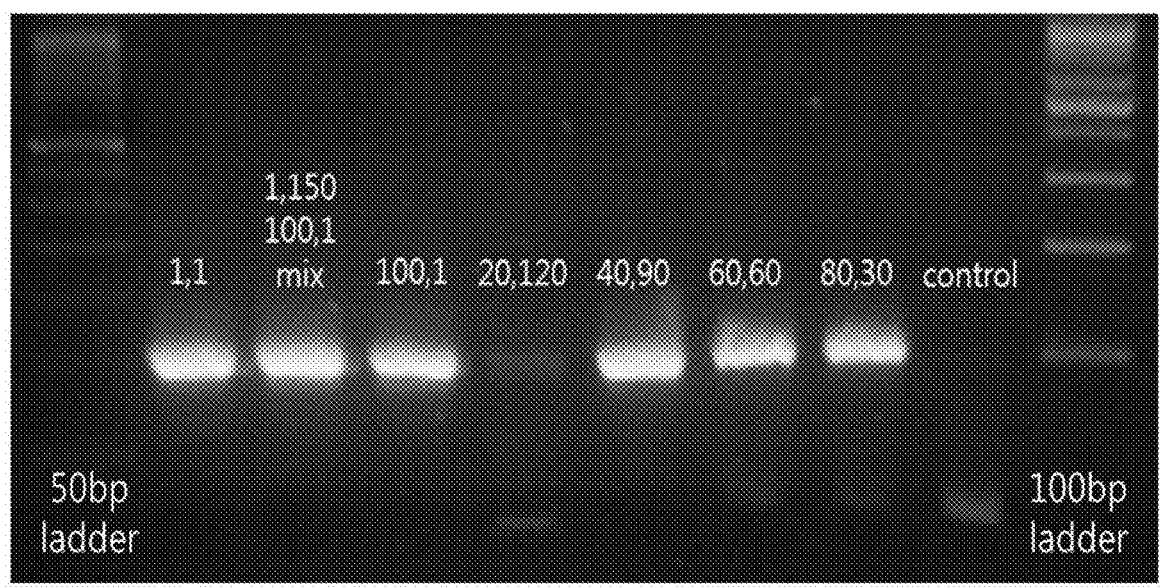

[Fig. 13]

file name : 55-1 8 (55,1) -> probe num 8101 , (55,1) , 13mer barcode , 1 deletion insert-> TGCGTGTCTCCGACTCAG GAGATATGAGTAT CGCCAGTGTGCTGGAATT

```
Query  405001  TGCGTGTCTCCGACTCAGGAGATATGAGTATCGCCAGTGTGCTGGAATT  405050
               ||||||||||||||||||||||||||||||| |||||||||||||||||
Sbjct  1       TGCGTGTCTCCGACTCAGGAGATATGAGTATC-GCCAGTGTGCTGGAATT  49
``` file name : 95-5 6 (95,1) -> probe num 14101, (95,1) , 13mer barcode , 1 mismatch

TGCGTGTCTCCGACTCAG GTGCAGGCATAACG CGCCAGTGTGCTGGAATT

```
Query  705001  TGCGTGTCTCCGACTCAGGTGCAGGTATAACGCGCCAGTGTGCTGGAATT  705050
               ||||||||||||||||||||||||| ||||||||||||||||||||||||
Sbjct  1       TGCGTGTCTCCGACTCAGGTGCAGGCATAACGCGCCAGTGTGCTGGAATT  50
``` file name : 85-1 6 (85,1) -> probe num 12601, (85,1) , 13mer barcode , 1 deletion

TGCGTGTCTCCGACTCAGAAGGGTGATCAAGCGCCAGTGTGCTGGAATT

```
Query  630001  TGCGTGTCTCCGACTCAGAAGGGTAGATCAAGCGCCAGTGTGCTGGAATT  630050
               |||||||||||||||||||||||| |||||||||||||||||||||||||
Sbjct  1       TGCGTGTCTCCGACTCAGAAGGGT-GATCAAGCGCCAGTGTGCTGGAATT  49
```

[Fig. 14]

ys2 1
TGCGTGTCTCCGACTCAGTGAGCTGTCTTGTTCGCCAGTGTGCTGGAATT

| Identities | Gaps |
|---|---|
| 50/50(100%) | 0/50(0%) |

```
Query  4451   TGCGTGTCTCCGACTCAGTGAGCTGTCTTGTTCGCCAGTGTGCTGGAATT  4500
              ||||||||||||||||||||||||||||||||||||||||||||||||||
Sbjct  1      TGCGTGTCTCCGACTCAGTGAGCTGTCTTGTTCGCCAGTGTGCTGGAATT  50
```

METHOD OF ISOLATING BIOCHEMICAL MOLECULES ON MICROARRAY SUBSTRATE

CROSS REFERENCE TO PRIOR APPLICATIONS

This application is a National Stage Application of PCT International Patent Application No. PCT/KR2013/011362 filed on Dec. 9, 2013, under 35 U.S.C. § 371, which claims priority to Korean Patent Application No. 10-2012-0142009 filed on Dec. 7, 2012, which are all hereby incorporated by reference in their entirety.

TECHNICAL FIELD

The present invention relates to a method of isolating biochemical molecules on a microarray substrate and a system of isolating the molecules.

BACKGROUND ART

Microarray synthesis technology is technology for simultaneously synthesizing a variety of different biochemical molecule types in parallel. A variety kinds of biochemical molecules are fixed while maintaining intervals of approximately several centimeters (cm) to several micrometers (um) on a solid substrate of a synthesized microarray. The synthesized biochemical molecule libraries are used in a state of being fixed to the solid substrate or in a solution state after being removed from the substrate. For example, the synthesized biochemical molecule libraries are used in a variety of genetic information analysis such as genome sequencing, single nucleotide polymorphism (SNP) analysis, genome-wide association study (GWAS), gene expression analysis, and the like, and application of the biochemical molecule libraries has facilitated development of life science, biotechnology, and biochemistry fields related to gene function analysis through shRNA library manufacture and screening, gene synthesis, and the like as an essential element. However, a method of efficiently isolating different kinds of molecules constituting a synthesized library was not introduced in most of the fields. Accordingly, in generally cases in which the synthesized library was used, the different kinds of biochemical molecules must be handled in a batch. At present, this is a major obstacle to extend application of a biochemical molecule library.

For example, research of assembling genes using a DNA library synthesized on a microarray was reported in 2004 [Jingdong Tian et al., Accurate multiplex gene synthesis from programmable DNA microchips, *Nature* 432, 1050-1054 (2004)]. However, due to complexity of different DNA sequence types mixed in a solution, it has been difficult to scale up the research to an economical scale. In the case of a DNA library among biochemical molecule libraries, when specific sequences are selectively amplified using specific primers through polymerase chain reaction (PCR), the same effects as isolation of different kinds of sequences can be provided. Successful gene assembly through such a method was reported [Sriram Kosuri et al., Scalable gene synthesis by selective amplification of DNA pools from high-fidelity microchips, *Nature Biotechnology* 28, 1295-1299 (2010)]. However, it is economically infeasible to applying such a method to all of different sequences and the method is only applicable to DNA library. That is, disadvantageously, the method cannot be applied to peptide or protein libraries. Therefore, the present inventors suggest technology of selectively isolating and collecting only desired biochemical molecules existing on specific spots among synthesized biochemical molecules on a microarray so as to overcome such technical limitations and individually apply different kinds of biochemical molecules.

DISCLOSURE

Technical Solution

In accordance with an aspect of the present invention, the above and other objects can be accomplished by the provision of a method of isolating biochemical molecules on a microarray substrate, the method including providing a microarray substrate to which clusters of different kinds of biochemical molecules being classified by individual spot units are attached, the individual spots being regularly arranged thereon; obtaining location information of the individual spot in which a desired cluster among clusters of the biochemical molecules locates; locating an extraction tool for applying energy to isolate the desired cluster according to the location information; and isolating the desired cluster from the microarray substrate by applying energy in a contact or non-contact manner using the extraction tool.

In accordance with another aspect of the present invention, there is provided a system for isolating biochemical molecules on a microarray including a stage equipped with a microarray substrate to which clusters of different kinds of biochemical molecules being classified by individual spot units are attached, the individual spots being regularly arranged on the microarray substrate; an extraction device for applying energy in a contact or non-contact manner to isolate a desired cluster among clusters of the biochemical molecules from the microarray substrate; and a control device to locate a specific area of the microarray substrate such that the area corresponds to the extraction device so as to isolate the desired cluster.

Advantageous Effects

The present invention relates to a method of individually isolating biochemical molecules on a microarray substrate and a system therefor. Although technology for synthesizing a variety kinds of molecules on a microarray substrate has been continuously developed, technology for efficiently isolating the synthesized molecules has not been developed. Accordingly, a microarray was restrictively used and application efficiency thereof was disadvantageously low in specific cases. Effects of isolating a substrate portion located in a specific spot with a microarray are the same as those of isolating selectively specific biochemical molecules from a library. Subsequently, library constituents may be individually used by spotting selectively collected biochemical molecules at sufficient physical intervals for separate postprocessing, or placing specific structure between the molecules such as the molecules are not mixed. As a result, complexity of biochemical molecules is reduced and, thus, the library may be more easily used, thereby increasing efficiency of chemical reaction. Therefore, application of a microarray can be more extended through the present invention. And the frequency of utilizing microarray can be more increased in previously used fields such as targeted resequencing, gene synthesis and so on.

DESCRIPTION OF DRAWINGS

The above and other objects, features and other advantages of the present invention will be more clearly understood from the following detailed description taken in conjunction with the accompanying drawings, in which:

FIG. 1 is a process flow chart illustrating an isolation method according to one embodiment of technology disclosed in the present specification;

FIG. 2 is a schematic diagram illustrating an isolation process according to one embodiment disclosed in the present specification;

FIG. 3 illustrates a method of isolating biochemical molecules on a microarray substrate according to one embodiment disclosed in the present specification;

FIG. 4 is a schematic diagram illustrating a system for isolating biochemical molecules on a microarray according to one embodiment disclosed in the present specification;

FIG. 5 is a schematic diagram illustrating a principle of isolating biochemical molecules on a microarray;

FIG. 6 illustrates a variety of embodiments of extracting desired biochemical molecules using a system for isolating biochemical molecules on a microarray;

FIG. 7 illustrates embodiments of DNA sequences used in experiments;

FIG. 8 illustrates a portion of a substrate, to which biochemical molecules are connected, separated due to energy applied by a system for isolating biochemical molecules on a microarray;

FIG. 9 illustrates a different biochemical molecule library bound by synthesized biochemical molecule on a microarray;

FIG. 10 illustrates isolation of synthesized biochemical molecules on a microarray and other biochemical molecule libraries bound by the biochemical molecules when a portion of a substrate, to which the biochemical molecules are connected, is separated due to energy applied by a system for isolating biochemical molecules on a microarray;

FIG. 11 illustrates a result proving that isolated DNA may be stably amplified without biochemical mutation despite of irradiation of pulse laser when biochemical molecules, particularly DNA, on a microarray were separated using the system;

FIG. 12 illustrates a result proving that only desired biochemical molecules among entire molecules on a microarray may be selectively isolated and amplified;

FIG. 13 illustrates a result proving that only desired DNA sequences among different DNA sequences on a microarray may be selectively isolated and the isolated DNA sequences are matched with the desired DNA sequences; and FIG. 14 illustrates a result proving that only desired DNA sequences among different DNA sequences on a microarray may be selectively isolated and the isolated DNA sequences are matched with the desired DNA sequences.

BEST MODE

Since physical coordinates of synthesized biochemical molecule libraries on a microarray are adjacent to each other such that it is hard to isolate individually through conventional method, the libraries were generally manipulated in a batch as in other library types. Technology disclosed in the present invention relates to technology for selectively isolating a portion of a microarray substrate with a microarray using microstructure manipulation technology so as to individually isolate and collect biochemical molecules. This is possible because desired biochemical molecules existing on the microarray are physically or chemically bound to the microarray substrate. Accordingly, effects of isolating a substrate portion having a specific spot with a microarray are the same as those of selectively isolating specific biochemical molecules from a library.

Subsequently, library constituents may be individually used by spotting selectively collected biochemical molecules at sufficient physical intervals such that separate postprocessing is possible, or placing a specific structure between the molecules such that the molecules are not mixed.

Hereinafter, the present invention will be described in detail by explaining embodiments of the invention with reference to the attached drawings. The following embodiments are provided to sufficiently communicate the scope of the present invention to those skilled in the art for illustrative purposes. Thus, the present invention is not limited to embodiments described below and may be specified by other embodiments. In addition, in drawings, widths, lengths, thicknesses, and the like of constituents may be exaggerated. Generally, drawings are explained in view of an observer and, when an element is referred to as being "on" another element, it can be "directly" on another element or can be "indirectly" formed such that an intervening element is also present.

According to one embodiment of the present invention, a method of isolating biochemical molecules on a microarray substrate is provided. FIG. 1 is a process flow chart illustrating an isolation method according to one embodiment of technology disclosed in the present specification. In step S1, clusters of different kinds of biochemical molecules are attached on the microarray substrate in individual spot units and the microarray substrate having individual spots regularly arranged thereon is provided. The expression "different kinds of biochemical molecules" may mean biochemical molecules being completely different based on general biochemical classification as a relation between nucleic acids and proteins. Alternatively, the expression "different kinds of biochemical molecules" may mean biochemical molecules having similar biochemical composition but being partially different, like adenine, guanine, cytosine, or thymine. Alternatively, the expression "different kinds of biochemical molecules" may mean nucleic acids molecules having different sequences but is not limited thereto.

The expression "cluster" means a gathering of molecules having an identical biochemical structure or a slightly modified structure through incomplete chemical reaction and the like. Generally, the cluster is classified into a spot unit and the spot may have a diameter or a major axis of 1 nm to 5 mm, preferably 100 nm to 1 mm, more preferably 300 nm to 1 mm, even more preferably 1 um to 500 um, particularly 5 um to 100 um.

The expression "individual spot" may have a structure that corresponds to the cluster in a ratio of preferably 1:1. The spot may have a diameter or a major axis of 1 nm to 5 mm, preferably 100 nm to 1 mm, more preferably 300 nm to 1 mm, even more preferably 1 um to 500 um, particularly 5 um to 100 um.

The expression "regularly arranged" means a shape arranged such that isosceles triangles, right-angled triangles, equilateral triangles, rhombuses, parallelograms, rectangles, squares, regular pentagons, regular hexagons, or regular octagons to regular 30-gons, preferably equilateral triangle, rectangles, squares, or regular hexagons, more preferably rectangles, squares, or regular hexagons is drawn by connecting the centers of spots, but is limited thereto and includes all designs having a regularity. An interval between the spots may be 1 nm to 5 mm, preferably 100 nm to 1 mm, more preferably 300 nm to 1 mm, even more preferably 1 um to 500 um, particularly 5 um to 100 um.

Generally, the substrate means a solid-state such as glass, silicon, and the like. However, in the present invention, the substrate includes gels such as polyacrylamide and agarose and is used as a wider concept.

The biochemical molecules on the microarray substrate may include nucleic acids, peptides, polypeptides, proteins, liposomes and combinations thereof. In addition, nucleic acids, which are structurally stable when energy is applied and may be amplified using an economical biochemical method, are desirably used.

The nucleic acids may include deoxyribonucleic acid (DNA), ribonucleic acid (RNA), peptide nucleic acid (PNA), locked nucleic acid (LNA), glycol nucleic acid (GNA), threose nucleic acid (TNA), xeno nucleic acid (XNA), synthetic nucleic acids, modified nucleic acids and combinations thereof. DNA or RNA is preferably used with the consideration of its structural stability when energy is applied and biotechnological utilization of extracted biochemical molecules.

The biotechnological utilization of the molecules may include amplification of DNA or RNA. Amplification of DNA or RNA may be carried out through a method using a polymerase such as polymerase chain reaction (PCR), in vitro transcription, reverse transcription, linear amplification, multiple displacement amplification (MDA), intracellular infusion, intracellular cloning, or combinations thereof.

A 3' terminal of the nucleic acid may be fixed on the microarray substrate via a linker. The linker stably fixes molecules through a covalent bond. In addition, the method of fixing the 3' terminal on the microarray substrate via the linker may further extend nucleic acid types which may be synthesized, when compared to a method of fixing a 5' terminal on a substrate via a linker. This is because of, in most phosphoramidite monomers for nucleic acid synthesis, 3' terminals of synthesized nucleic acids are fixed on the microarray substrate via a linker according to a chemical synthesis method.

The microarray may be manufactured through a variety of in situ synthesis methods such as inkjet printing [A. P. Blanchard et al., High-density oligonucleotide arrays, *Biosensors & Bioelectronics* 11, 687-690 (1996)], photolithography [Stephen P. A. Fodor et al., Light-directed, spatially addressable parallel chemical synthesis, *Science* 251, 767-773 (1991)], an electrochemical method [Donald D. Montgomery, U.S. Pat. No. 6,093,302, Electrochemical solid phase synthesis], and the like. In addition, the microarray may be manufactured through a spotting method in which each of different kinds of molecules is individually placed on each individual site on a substrate [Mark Schena et al., Quantitative monitoring of gene expression patterns with a complementary DNA microarray, *Science* 270, 467-470 (1995)], a large area transfer method, or a replication method [Haohao Lin et al., Replication of a DNA microarray, *JACS* 127, 11210-11211 (2005), Haohao Lin et al., Replication of a DNA microarray from zip code masters, *JACS* 128, 3268-3272 (2006)]. In the case of a microarray manufactured through transfer or replication, properties of the microarray substrate may be different from properties of an original microarray, whereby efficiency may be advantageously increased when energy is applied thereto at an extraction step. In addition, through replication of the microarray, a unit cost may be lowered and a plurality of the same spots may be advantageously manufactured.

As described above, a microarray type is not specifically limited so long as the microarray has a type where biochemical molecules are attached to a substrate surface through a covalent bond, adsorption, or the like. However, a microarray manufactured using a solid-phase synthesis method, in which monomers of biochemical molecules are sequentially synthesized on a solid support, is preferably used. In solid-phase synthesis, parallel process is possible and volumes of reagents used in the synthesis can be minimized, whereby amplifying after isolating individual spots of the synthesized microarray is more economical than a general biochemical molecule synthesis method. For example, a method of isolating each DNA after manufacturing a DNA microarray through solid-phase synthesis is more economical than a method of synthesizing each DNA through a controlled pore glass (CPG)-column on nanomole scale or greater.

The solid-phase synthesis may include solid-phase synthesis of biochemical molecules using phosphoramidite, FMOC, BOC, or the like, preferably solid-phase synthesis of nucleic acids using phosphoramidite. Since the solid-phase synthesis of nucleic acids using the phosphoramidite has the highest coupling efficiency among presently used solid-phase synthesis methods, desired biochemical molecules may be correctly synthesized. In addition, in the case that nucleic acids are isolated from the microarray, efficiency of the technology disclosed in the present specification increases and efficiency of biochemical molecules after extraction thereof may be maximized.

Materials such as other molecules or other cells may be introduced to the microarray through coupling or adsorption via the biochemical molecules synthesized on the microarray. Since the biochemical molecules synthesized on the microarray may have different molecule structures, different libraries may be distinguished based on chemical characteristics due to structural differences. Therefore, effects of isolating a different library may be provided by isolating individual spots of the microarray, based on the differentiation. The different library means a library of biochemical molecules such as nucleic acids, modified nucleic acids, proteins, peptides, liposomes, or the like, a chemical molecules library such as small molecules or the like, a virus library, or a variety of cellular libraries such as *E. coli*, yeasts, leukocytes, cancer cells, stem cells, and the like. In addition, the different library may include a library of materials with volumes of 1 aL to 1 uL. As desirable combinations of the biochemical molecules synthesized on the microarray and the different library, there are a combination of nucleic acids and nucleic acids, a combination of nucleic acids and nucleic acid binding proteins, a combination of nucleic acid binding proteins and nucleic acids, a combination of nucleic acids and cells having nucleic acid binding protein displayed on a surface thereof, and a combination of nucleic acids and viruses having nucleic acid binding proteins on surfaces thereof. Above list of combinations have the advantage to be sorted with the knowledge of its composition and its biochemical characteristics. Examples of the nucleic acid binding proteins include zinc fingers, transcription activator-like effectors (TALE), and the like. More broadly, examples of the nucleic acid binding proteins include RecA, Cas9, transposomes, and the like which bind to DNA or RNA via DNA or RNA.

The microarray substrate may be a substrate replicated from a template, a substrate including a sacrificial layer therein, a substrate surface-coated with a sacrificial layer, a substrate undergoing phase transition occurred through electromagnetic field, or a combination thereof. These substrates may have advantageously improved efficiencies when energy is applied thereto at an extraction step. It is desirable to place a sacrificial layer on the microarray substrate to increase extraction efficiency of biochemical molecule and at the same time, minimize the damage through sacrificial layer absorbs energy applied to biochemical molecules. A glass could be used as a sacrificial layer by lowering transmittance or increasing absorbance to absorb the energy. Or silicon could also be used by lowering transmittance or increasing absorbance to absorb the energy.

In addition, the sacrificial layer may be coated on a surface of a solid such as glass, silicon, or the like and exist inside a solid such as glass, silicon, or the like, but the present invention is not limited thereto. The substrate exhibiting phase transition occurred due to electromagnetic field means a solid substrate temporarily or permanently liquefied, vaporized, or converted to plasma by the electromagnetic field. The substrate replicated from the template means a microarray substrate manufactured through large area transfer or replication [Haohao Lin et al., Replication of a DNA Microarray, *JACS* 127, 11210-11211 (2005), Haohao Lin et al., Replication of a DNA Microarray from Zip Code Masters, *JACS* 128, 3268-3272 (2006)].

In step S2, a piece of location information of a desired cluster among the clusters of the biochemical molecules spotted on the microarray substrate is obtained. Although time of determining location information of the biochemical molecules spotted on a microarray substrate is not specifically limited, the location information may be preferably determined before synthesis of the biochemical molecules. Although the location information may be provided in a variety of types such as documents, computer files, and the like, the location information is preferably provided in a computer file type to interwork with a control device mainly composed of a computer.

In addition, since the location information is an imaginary value, a process of searching for an actual spot of the desired cluster is preferably performed before step S3. In most cases, since the microarray is regularly arranged, an actual spot may be easily confirmed by calculating a distance from a control point when the control point is exactly set. The control point may be a corner of the microarray substrate, a specific mark on the substrate, or a specific spot. In addition, when a specific spot is searched for, a marking method using fluorescent molecules and an imaging process through a microscope may be further included.

In step S3, an extraction tool for applying energy to isolate the desired cluster depending on the location information. Examples of the extraction tool include a variety of devices capable of applying energy in a contact or non-contact manner of step S4 described below. The extraction device may be combined with a movable equipment to provide mobility. The movable equipment may be an automated motor and may be manipulated with precision of preferably 1 mm or less, more preferably 100 um or less, even more preferably 5 um or less. Since an interval between spots is 5 um to 100 um in most microarrays, the gearing which may be manipulated with a precision of particularly 5 um or less may accurately isolate desired clusters in most microarrays.

Next, in step S4, energy is applied using the extraction tool in a contact or non-contact manner so as to isolate the desired cluster from the microarray substrate. Examples of the contact manner include pipetting and micro grabbing and examples of the non-contact manner include pulse laser irradiation and ultrasonic wave application. Preferably, selective collection of biochemical molecules present on a specific spot is carried out by applying energy in a non-contact manner so as to isolate the desired cluster from the microarray substrate. In this case, cross contamination may be prevented.

Preferably, pulse laser ablation or radiation pressure ejection may be performed through pulse laser irradiation among non-contact manners. In this case, a portion of the microarray substrate is isolated and fragments of the isolated substrate proceed in an opposite direction of the substrate. In this regard, since progress pathways of the fragments are not greatly different, the fragments may be more easily collected. In addition, according to one embodiment, the pulse laser may be used to cut the linkers between the biochemical molecules and the microarray substrate, the biochemical molecules, and the like.

The pulse laser may have a wavelength of 10 to 10,000 nm, preferably 20 to 5,000 nm, more preferably 100 to 2,000 nm. In ranges including the visible light spectrum, the electromagnetic field does not greatly affect optical components and energy may be transmitted to the microarray substrate. In addition, the system may be easily realized since most commercial pulse lasers operate in the ranges, and the technology disclosed in the present invention may be carried out without significant system modification when the substrate using the sacrificial layer is used.

The pulse laser may have a pulse duration of 1 as to ms, preferably 1 fs to 100 ns. By applying the pulse duration, a progression pathway is more constant when pulse laser ablation due to the pulse laser occurs and, thus, collection may be more easily carried out. In addition, by applying the pulse duration, damage to the biochemical molecules on the microarray substrate may be reduced when pulse laser ablation occurs, whereby efficiency may be increased when post processing of the isolated biochemical molecules is performed.

The step of isolating the desired cluster from the microarray substrate includes a process of moving the desired cluster to a reservoir. The moving process is a process necessary to store the isolated biochemical molecules and use the molecules when reaction with other reaction products is necessary. The reservoir may include a container manufactured to cause physical or chemical reaction or to observe the same. In addition, the reservoir may include a container manufactured to store biochemical molecules. The reservoir has a volume of 1 aL to 1 L, preferably 1 fL to 10 mL, more preferably 1 pL to 500 uL and such volumes correspond to a reaction volume in which postprocessing of biochemical molecules isolated by biochemical reaction may be most easily performed. In addition, the reservoir may have, for example, a microwell array structure in which the volume of each well is 1 pL to 1 uL [David K. Wood et al., Single cell trapping and DNA damage analysis using microwell arrays, *PNAS* (2010)], so as to minimize waste of reagents by reducing a reaction volume during chemical reaction of the isolated biochemical molecules. In addition, by using the microwell array structure, reaction rates and efficiencies in some reactions may be improved.

The step of isolating the desired cluster from the microarray substrate is carried out in a manner that the cluster is partially or entirely transferred to the at least one reservoir. By isolating a portion of the cluster, the corresponding biochemical molecules may be used at least once and, thus, the number of synthesized biochemical molecules may be reduced. In addition, a plurality of the desired clusters may be isolated from one reservoir and, thus, chemical reaction among biochemical molecules may be induced.

The method of isolating the biochemical molecules on the microarray substrate according to one embodiment of the present invention may further include a step of amplifying the desired cluster isolated from the microarray substrate after the isolation step. The amount of biochemical molecules existing on a general microarray substrate may be insufficient to proceed chemical reaction in a generally used reservoir, a unit of which is uL. Therefore, application ranges of the isolated biochemical molecules may be extended by performing the amplification step after the isolation step, depending upon purposes of biochemical molecules. The desired cluster may be preferably nucleic acids since amplification of the nucleic acids is easier and more economical, when compared with other biochemical molecules or other libraries attached via the biochemical molecules. The amplified nucleic acids are preferably DNA or RNA. The DNA or RNA may be amplified through a method of using polymerase such as polymerase chain reaction (PCR), in vitro transcription, reverse transcription, linear amplification, multiple displacement amplification (MDA), intracellular infusion, intracellular cloning, or combinations thereof.

A method of isolating the biochemical molecules on the microarray substrate according to one embodiment of the present invention may further include sequencing the desired cluster or a chemical reaction product thereof isolated from the microarray substrate or using the same in gene synthesis. The desired cluster may be nucleic acids, preferably DNA. The chemical reaction product may be amplified biochemical molecules, preferably amplified nucleic acids, more preferably amplified DNA.

The isolated biochemical molecules or the biochemical molecules amplified after isolation may be used to prepare capture probes for target sequencing, and exome or whole exome sequencing (WES). The isolated biochemical molecules or the biochemical molecules amplified after isolation are preferably DNA or RNA. For example, when DNA molecules are present on the microarray, the DNA molecules are isolated and amplified, and the amplified DNA molecules are hybridized with gDNA through transcription or the like, only specific sequences may be selectively collected and, by analyzing the collected sequences, target sequencing or exome sequencing may be effectively performed. In particular, since individual capture probes are separated, capture efficiency may be intentionally controlled by controlling the concentration of each probe. If the amount of DNA molecules present on the microarray is sufficient, processes after hybridization may be carried out without amplification.

The isolated nucleic acids may be assembled into a gene using at least one of the amplification, ligation, assembly PCR, isothermal assembly [Daniel G Gibson et al., Enzymatic assembly of DNA molecules up to several hundred kilobases, *Nature Methods* 6, 343-345 (2010)], and pairwise assembly [William J. Blake et al., Pairwise selection assembly for sequence-independent construction of long-length DNA, *Nucleic Acids Research* 38, 2594-2602 (2010)].

FIG. 2 is a schematic diagram illustrating an isolation process according to one embodiment disclosed in the present specification. (a) represents different kinds of biochemical molecules synthesized on a microarray substrate. The biochemical molecules are fixed on the microarray substrate via a covalent bond, adsorption, or the like. As shown in (b), pulse laser ablation or radiation pressure ejection occurs when pulse laser is irradiated to the desired location of the microarray substrate through a condenser or lens and, thus, a portion of the microarray substrate is isolated from the whole substrate. As a result, the isolated microarray substrate is dropped toward a reservoir and, since biochemical molecules corresponding to the desired location are fixed on the isolated substrate, desired biochemical molecules may be isolated into a reservoir. (b) may also be performed in cases of other desired biochemical molecules, which is represented in (c).

FIG. 3 illustrates the method of isolating the biochemical molecules on the microarray substrate according to one embodiment disclosed in the present specification. Referring to FIG. 3(a), one kind of biochemical molecule may be entirely isolated in a reservoir. In addition, referring to (b-1) and (b-2), the same biochemical molecules may be isolated in different reservoirs as described above. By partially isolating the cluster, relevant biochemical molecules may be used at least once and, thus, the number of synthesized biochemical molecules may be reduced. In addition, a plurality of biochemical molecules may be simultaneously isolated in one reservoir as illustrated in (c) or isolated by time intervals as illustrated in (d-1) and (d-2). By isolating a plurality of desired clusters into one reservoir, chemical reaction among biochemical molecules may be induced.

According to another embodiment of the present invention, a system for isolating biochemical molecules on a microarray is provided. FIG. 4 is a schematic diagram illustrating a system for isolating biochemical molecules on a microarray according to one embodiment disclosed in the present specification. The system suggested in the present invention includes a stage equipped with a microarray substrate to which clusters of different kinds of biochemical molecules being classified by individual spot units are attached, the individual spots being regularly arranged on the microarray substrate; an extraction device for applying energy in a contact or non-contact manner to isolate a desired cluster among clusters of the biochemical molecules from the microarray substrate; and a control device to locate a specific area of the microarray substrate such that the area corresponds to the extraction device so as to isolate the desired cluster.

According to one embodiment, the extraction device may include a pulse laser light source and a condenser. The condenser is preferably an optical lens which is used to collect pulse laser energy and, at the same time, to image the microarray substrate. The pulse laser may exactly irradiate a spot to be isolated on the substrate at a desired time point, which is performed by controlling pulse laser emission using a control device such as a general computer. The optical lens may have a magnification of 2× to 100×, preferably 10× to 40×. By using the magnifications, energy suitable for isolation may be transmitted to the microarray substrate and prevent the lens and the microarray substrate from contacting each other or from departing from a focal distance.

According to one embodiment, in the system of isolating the biochemical molecules on the microarray, at least one of the stage, the extraction device, and the control device may be manipulated with a precision of 1 mm, preferably 100 um, more preferably 5 um or less. Since an interval between spots is 5 um to 100 um in most microarrays, the stage, the extraction device, and the control device which are manipulated with a precision of 5 um or less may exactly isolate a desired cluster in most microarrays.

According to one embodiment, the system may further include an imaging device for observing the microarray substrate so as to isolate the desired cluster. The imaging device may be composed of at least one of an optical lens, a light source, and an image sensor. The optical lens may be included in an extraction device and, as needed, the optical lens may be additionally used separately.

The wavelength of the light source may be 10 nm to 10,000 nm, preferably 50 nm to 2,000 nm, more preferably 100 nm to 1,500 nm. In the wavelength ranges, the microarray may be most easily observed or measured using fluorescence or visible light. As the light source, for example, a halogen lamp may be used.

As the image sensor, a charge-coupled device (CCD) is generally used, but the present invention is not limited thereto. In step S2, after obtaining location information of an individual spot in which a desired cluster among the clusters of the biochemical molecules on the microarray substrate is located, the imaging device may be used to confirm whether the spot is present in the location. In addition, the imaging device may be used to confirm that, in step S3, an extraction tool for applying energy is exactly located such that the desired cluster is isolated according to the location information. In addition, the imaging device may be used to confirm whether, in step S4, the desired cluster isolated from the microarray substrate is present within the reservoir.

According to one embodiment, a separate stage equipped with the reservoir for collecting the isolated desired cluster may be further included. The stage may be manipulated with a precision of 1 mm or less, preferably 100 um or less, more preferably 1 um or less. The separate stage equipped with the reservoir may facilitate utilization of the isolated biochemical molecules and the stage having precision of 1 um or less may isolate the biochemical molecule into a reservoir having a 1 pL to 1 uL microwell array structure.

FIG. 4 illustrates one embodiment of the system of isolating the biochemical molecules on the microarray. The system is divided into an upper system and lower system. The upper system is controlled by a computer and composed of an upper stage (Motorized XY stage), the microarray substrate is connected to a lower portion of which, pulse laser, and an upper imaging device.

The upper system composed of an afocal optical system may observe spots of the microarray substrate through upper and lower axis movement of the optical lens and, at the same time, control and determine spot location of the pulse laser. The optical lens also functions as a condenser since an imaging plane and a pulse laser spot are set in a similar location therein. The pulse laser spot means a location where pulse laser energy is concentrated through the condenser. When location of the pulse laser spot is input to an algorithm, a physical location, at which each corresponding biochemical molecule is present, is extracted by comparing pixel data transferred via CCD and a physical location of a spot on an actual microarray. When location information of a microarray spot having desired specific biochemical molecules is provided to the upper stage equipped with the microarray substrate, a pulse laser spot moves to a relevant spot. At the same time, the lower stage and a PCR plate as a reservoir which is a relevant substrate equipped thereto are located most closest to the upper substrate in a Z axis direction such that wells of the reservoir or the PCR plate receive sequentially isolated microarray fragments in a lower position.

A pulse laser beam concentrated through the condenser is irradiated to the microarray substrate and the relevant spot of the microarray substrate is pushed to the PCR plate functioning as a lower reservoir through expansion pressure due to pulse laser ablation or radiation pressure. The condenser may be an optical lens and have, for example, a magnification of 2× to 100×. A lower system has a PCR tube rack or the PCR plate functioning as a reservoir attached in an upper direction of the lower system and is composed of a lower stage (Motorized XYZ stage) movable in a Z axis direction and a lower imaging device. In the lower imaging device, a reservoir, in which penetration imaging is possible, may be used so as to optically confirm when the fragments isolated from the microarray are collected, or so as to determine a physical reference location of the well. For example, examples of the reservoir include a variety of container types such as a flat bottom reservoir and a flat bottom PCR plate which are manufactured from a transparent plastic material. A pathway of light derived from a light source of the lower imaging device is less affected by using the plane bottom of the reservoir and, thus, imaging may be easily performed. In addition, when observed through the upper imaging device due to microarray characteristics, whether the substrate is isolated by applying sufficient energy to the microarray substrate may be easily confirmed only through appearance of the microarray substrate. Thus, the lower imaging device for providing penetrated light of the imaging device may be used.

For example, in the case of the microarray substrate in which the substrate is isolated, isolation of the substrate may be judged using change of light penetration.

FIG. 5 is a schematic diagram illustrating a principle of extracting a solid support. Referring to FIG. 5, when pulse laser beams are concentrated through an optical lens, expansion pressure due to pulse laser ablation or radiation pressure (radiation pressure ejection) functions in a pulse laser spot and, thus, some of the substrate is isolated and released from the microarray substrate.

A variety of methods may be used to isolate the biochemical molecules on the microarray substrate using pulse laser. Examples of an extraction method thereof include a method of radiating pulse laser beams to the microarray substrate having synthesized biochemical molecules, a separate microarray substrate including biochemical molecules, or a microarray substrate having another library bound or adsorbed via the biochemical molecules.

FIG. 6 illustrates a variety of examples extracting biochemical molecules or a corresponding spot using the biochemical molecule isolation system on the microarray substrate. Referring to FIG. 6, (a) is a general manner in which a spot of biochemical molecules located in a lower portion of the microarray substrate is light irradiated at the rear and downwardly pushed. In (b) similar to (a), damage of biochemical molecules is minimized by placing a sacrificial area irrelevant to reaction of biochemical molecules between a biochemical molecules and a microarray substrate and irradiating the sacrificial area with concentrated light. In (c), which is the same as (a), irradiated light travels from a lower direction to an upper direction and a new substrate in which fragments of a microarray having biochemical molecules fixed thereon are moved has adhesion, whereby the spot of the fragments and biochemical molecules is fixed and not dropped therefrom due to gravity. (d) illustrates a method of correcting at least one microarray fragment having the same biochemical molecule type or different kinds of biochemical molecules in one tube. (e) illustrates a method of correcting a variety kinds of microarray fragments in one tube. (f) illustrates a method of a concentrating pulse laser to a front side having wells and extracting to a reservoir, in which penetration imaging is possible, locating in a direction the same as a irradiation direction of incident light, when a microarray substrate having biochemical molecules fixed thereon is optically opaque and, thus, backward irradiation is impossible. A concentrated spot of the pulse laser is intentionally outside the center of a well or the center of a microbead so as to increase isolation efficiency of the microbead. In (g), a separate substrate such as a translucent substrate or the like is further introduced for easy extraction when the microarray substrate is optically opaque. The separated substrate may be composed of an adhesive and indurative material so as to transfer a spot, in which desired biochemical molecules are synthesized, from the microarray substrate. The spot having the desired biochemical molecules synthesized therein is separated from the separate substrate while maintaining location information, and then may be extracted by the same method as in (a) to (e). In addition, the separate substrate includes a substrate replicated from a template, a substrate including a sacrificial layer therein, a substrate surface-coated with a sacrificial layer, a substrate undergoing phase transition occurred by electromagnetic field or combinations thereof. The substrates have an advantage that efficiency is increased when energy is added in an extraction step. Preferably, a sacrificial layer may be placed on the microarray substrate, whereby extraction efficiency is increased by energy absorption of the sacrificial layer and substantially simultaneously damage of the biochemical molecules may be minimized by reducing the total amount of energy imparted to the biochemical molecules. The sacrificial layer may be glass in which absorption of energy is increased by reducing transmittance or increasing absorbance or silicon in which absorption of energy increased by decreasing transmittance or increasing absorbance. In addition, the sacrificial layer may be coated on a solid surface such as glass, silicon or the like and may exist within a solid such as glass, silicon or the like, but the present invention is not limited thereto. The expression "substrate undergoing phase transition occurred by electromagnetic field" means a solid substrate temporarily or permanently liquefied, vaporized or converted to plasma by electromagnetic field. The expression "substrate replicated from a template" means a microarray substrate manufactured through large area transfer or replication [Haohao Lin et al., Replication of a DNA microarray, *JACS* 127, 11210-11211 (2005), Haohao Lin et al., Replication of a DNA Microarray from Zip Code Masters, *JACS* 128, 3268-3272 (2006)].

In addition to the examples, there are a variety of methods of isolating biochemical molecules on a microarray substrate using pulse laser.

FIG. 7 illustrates examples of DNA sequences in the present experiment. So as to amplify isolated DNA after isolating the DNA on a microarray substrate, universal sequences were attached to both ends of the sequences, whereby different sequences may be amplified using one primer. The universal sequences are a 5' terminal of TGCGTGTCTCCGACTC and a 3' terminal of CGCCAGTGTGCTGGAATT. However, even when universal sequences are present only at a 5' terminal, a 3' terminal or a spot portion not being a terminal of sequences, or the universal sequences are not present, the technology in the present invention may be applied.

FIG. 8 illustrates a portion of a substrate, to which biochemical molecules are connected, separated due to energy applied by a system for isolating biochemical molecules on a microarray. The microarray substrate was composed of glass and irradiated using a pulse laser having a wavelength of 532 nm and a nanosecond duration. A portion marked with a dotted circle is a microarray substrate portion partially isolated by irradiation with the pulse laser.

FIG. 9 illustrates a different biochemical molecule library bound by synthesized biochemical molecule on a microarray. The biochemical molecules synthesized on the microarray are DNA and the different biochemical molecule libraries are DNAs linked to fluorescein amidite (FAM), which is a kind of fluorescence molecule, at a 5' terminal thereof. A portion of the DNA synthesized on the microarray has sequences complementary to partial sequences of the different DNA library. Accordingly, fluorescence is generated in spots having sequences complementary to the different DNA library, whereby it can be proved that the different biochemical molecule libraries bind to the microarray via synthesized biochemical molecules.

FIG. 10 illustrates isolation of synthesized biochemical molecules on a microarray and other biochemical molecule libraries bound by the biochemical molecules when a portion of a substrate, to which biochemical molecules are connected, is separated due to energy applied by a system for isolating biochemical molecules on a microarray. When comparing figures of a left row and middle row, it can be confirmed that, when energy is applied to a portion of the substrate having the biochemical molecules connected thereto with a pulse laser, fluorescence of a portion of the substrate disappears. On the other hand, since fluorescence is continuously observed in the other areas except for the substrate portion, it can be confirmed that the substrate portion was isolated from the microarray due to the pulse laser irradiated to the substrate portion and DNA including the fluorescence molecules on the substrate was also isolated. Isolation of the microarray substrate may be confirmed from figures at a right row.

FIG. 11 illustrates a result proving that isolated DNA may be stably amplified without biochemical mutation despite irradiation with a pulse laser when biochemical molecules, particularly DNA, on a microarray were isolated using the system. In FIG. 11, polymerase chain reaction of a control was carried out only using primers corresponding to universal sequences. In FIG. 11, 10× and 1× means a frequency of pulse laser irradiation of used to isolate DNA on the microarray substrate. In FIG. 11, a 100 bp ladder is a biochemical molecule which is separated in a 100 bp unit from 100 base pairs (bp) to 1000 bp for standard setting. Light having specific wavelength such as UV causes DNA damage such as a thymine dimer and, when the DNA damage is induced, efficiency of biochemical reaction such as polymerase chain reaction is reduced. From a result of FIG. 11, it can be confirmed that the DNA molecules isolated from the desired spot may be amplified although pulse laser is irradiated 10 times (10×) and, thus, the pulse laser did not cause critical DNA damage. Such a result suggests that the pulse laser energy was concentrated only to the microarray substrate and did not affect the biochemical molecules on the microarray substrate.

FIG. 12 illustrates a result proving that only desired biochemical molecules among biochemical molecules on a microarray may be selectively isolated and amplified. It can be confirmed that corresponding spot may be found, without imaging, only using location information of four spots (20,120), (40,90), (60,60) and (80,30) except for a control points (1,1), (1,150) and (100,1) marked with fluorescence and amplification of all of the four spots isolated through irradiation with the pulse laser is successful. When the four spots, which were distant from each other, among 15,000 spots located on a 100×150 array was irradiated with laser, DNA was separated from the irradiated spots and the separated DNA was amplified, which indicates that the technology disclosed in the present specification may be realized. In FIG. 12, polymerase chain reaction of a control was carried out only with primers corresponding to universal sequences. In FIG. 12, a 100 bp ladder is a biochemical molecule which is separated in a 100 bp unit from 100 base pairs (bp) to 1000 bp for standard setting.

FIG. 13 illustrates a result proving that only desired DNA sequences among different DNA sequences on a microarray may be selectively isolated and the isolated DNA sequences are the same as the desired DNA sequences. The desired DNA on the microarray substrate was isolated from the substrate through the biochemical molecule isolation, and then an amplified DNA was purified and then cloned, followed by Sanger sequencing. Most of the isolated DNA sequences were identical to sequences of one DNA among designed DNA in a ratio of 98% and different from sequences of the other DNA. Accordingly, it can be confirmed that the desired DNA molecules on the microarray substrate may be selectively isolated using the method disclosed in the present specification. 1 base error is caused by deletion, which is the most likely error to occur during microarray synthesis. Since DNAs used in an experiment of FIG. 13 have universal sequences at both sides thereof, the DNA may be amplified using one primer set although the DNA sequences are different. The universal sequences include TGCGTGTCTCCGACTC of a 5' terminal and CGCCAGTGTGCTGGAATT of a 3' terminal. Different 13 nucleotides (nt), which were denoted by a 13 mer barcode, are present in middles of the DNA sequences used in the experiment. (55,1), (95,1) and (85,1) Of FIG. 13 mean spots of DNA separated from the microarray substrate by irradiating a pulse laser. "Probe num" of FIG. 13 is an arbitrary number assigned for convenient subsequent works when the isolated DNA was designed and each "Probe num" corresponds to specific DNA sequences. From the result of FIG. 13, it can be confirmed that each DNA present in three different spots on the microarray substrate may be stably isolated and amplified, and the amplified sequences are almost identical to the initial design.

FIG. 14 illustrates a result proving that only desired DNA sequences among different DNA sequences on a microarray may be selectively isolated and the isolated DNA sequences are the same as the desired DNA sequences. The desired DNA on the microarray substrate was isolated from the substrate through the biochemical molecule isolation method, and then an amplified DNA was purified and then cloned, followed by Sanger sequencing. Most of the isolated DNA sequences were identical to sequences of one DNA among designed DNA in a ratio of 98% and different from sequences of the other DNA. Accordingly, it can be confirmed that the desired DNA molecules on the microarray substrate may be selectively isolated using the method disclosed in the present specification. In FIG. 14, the expression "Query" corresponds to designed sequences of the DNA and the expression "Sbjct" corresponds to a result of Sanger sequencing. In FIG. 14, the expression "ys2 1" means a title of isolated desired DNA and was arbitrarily designated for experimental convenience. In FIG. 14, DNA sequences, TGCGTGTCTCCGACTCAGTGAGCTGTCTTGTTCGCCAGTGTGCTGGAATT, illustrated below a DNA title, "ys2 1" means sequences of the isolated desired DNA.

When the technology disclosed in the present specification is used in gene assembly using synthesized DNA in a microarray, the synthesized DNA may be used as an assembly reaction material by selectively isolating and collecting specific DNA fragments so as to synthesize target genes among synthesized DNA fragments on the microarray. Accordingly, complexity decreases, thereby increasing assembly efficiency and economical.

The technology disclosed in the present specification may be used in target sequencing and manufacture of capture probes for exome or whole exome sequencing (WES). For example, when DNA molecules are present on a microarray and the molecules are isolated and hybridized with gDNA through amplification, transcription or the like, specific sequences may be selectively collected and, by analyzing the collected sequences, target sequencing or exome sequencing may be effectively carried out.

When the technology disclosed in the present specification is used in isolation of mRNA or cDNA library, specific mRNA or cDNA may be individually collected by separating spots in which individual probes are synthesized after synthesizing specific probe sequences, which may hybridize with specific mRNA or cDNA among mRNA or cDNA library, on a microarray and fixing the individual mRNA or cDNA on a specific location of the microarray via a probe through reaction of the microarray and the mRNA or cDNA library.

The technology disclosed in the present specification may be used for collecting error-free oligonucleotides. For example, random DNA barcodes having error-free oligonucleotides may be found by connecting the random DNA barcodes having arbitrary DNA sequences to individual oligonucleotides and amplifying the connected sequences, followed by storing some of the amplified products and sequencing some thereof [Hwangbeom Kim et al., 'Shot-gun DNA synthesis' for the high-throughput construction of large DNA molecules, *Nucleic Acids Research* 40, e140 (2012)]. When probes complementary to the random DNA barcodes are synthesized on a microarray and the synthesized probes are reacted with oligonucleotides, error-free oligonucleotides may be fixed on each specific spot. Subsequently, when a spot in which the individual probes are synthesized is isolated according to the present technology, error-free oligonucleotides among oligonucleotides may be selectively isolated.

When the technology disclosed in the present specification is used, a DNA binding protein library also may be isolated. When DNA binding proteins such as a transcription activator like effector (TALE), zinc finger and the like are reacted with a DNA microarray and individual spots of the reacted microarray are collected, proteins binding to specific DNA sequences may be selectively isolated.

Furthermore, when a virus library, in which a library of DNA binding proteins is displayed on virus surfaces, or a cellular library, in which a library of DNA binding proteins is displayed on cellular surfaces, is reacted with a DNA microarray and individual spots are collected, each virus or cell producing a specific DNA binding protein may be obtained. Since specific aptamers synthesized on the microarray are multiply used in the technology disclosed in the present specification, the technology may be used to isolate individual proteins.

The technology disclosed in the present specification may be used to individually isolate an RNA molecule library or a peptide molecule library synthesized in parallel on the microarray.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of isolating biochemical molecules on a microarray substrate, the method comprising:
providing a microarray substrate to which clusters of different kinds of biochemical molecules being classified by individual spot units are attached, the individual spots being regularly arranged thereon, wherein the microarray substrate is one of a substrate including a sacrificial layer, a substrate surface-coated with a sacrificial layer, and combinations thereof;

obtaining location information of the individual spot in which a desired cluster among clusters of the biochemical molecules locates;

locating an extraction tool for applying energy to selectively isolate the desired cluster according to the location information; and selectively isolating the desired cluster from the sacrificial layer of the microarray substrate by applying energy in a contact or non-contact manner using the extraction tool, such that the desired cluster is selectively and directly transferred to a selected well in a reservoir well plate below each of the individual spot units when the desired cluster is severed from the microarray substrate, wherein the microarray substrate is irradiated with a pulse laser to apply energy.

2. The method according to claim 1, wherein pulse laser ablation or radiation pressure ejection is performed by irradiation with the pulse laser.

3. The method according to claim 1, wherein the pulse laser has a wavelength of 10 to 10,000 nm.

4. The method according to claim 1, wherein the pulse laser has a pulse duration of 1 as to 1 ms.

5. The method according to claim 1, wherein the biochemical molecules comprise nucleic acids, polypeptides, peptides and combinations thereof.

6. The method according to claim 5, wherein the nucleic acids comprise DNA, RNA, PNA, LNA, GNA, TNA, XNA, synthetic nucleic acids, modified nucleic acids and combinations thereof.

7. The method according to claim 5, wherein a 3' terminal of the nucleic acids is fixed on the microarray substrate via a linker.

8. The method according to claim 1, wherein the microarray substrate is manufactured through solid-phase synthesis to sequentially synthesize monomers of the biochemical molecules on a surface of the microarray substrate.

9. The method according to claim 1, wherein other molecules or other cells are introduced to the microarray via the biochemical molecules synthesized on the microarray.

10. The method according to claim 1, wherein the isolating comprises transferring the desired cluster to a reservoir individually.

11. The method according to claim 10, wherein the isolating is performed by partially or entirely transferring the cluster to at least one reservoir individually.

12. The method according to claim 1, wherein the pulse laser is irradiated to sever a connection between the biochemical molecules and the microarray substrate.

13. The method according to claim 1, further comprising amplifying the desired cluster isolated from the microarray substrate.

14. The method according to claim 1, further comprising using the desired cluster isolated from the microarray substrate or a chemical reaction product thereof in a sequencing process or a gene synthesis process.

15. The method according to claim 1, wherein, in the step of selectively isolating the desired cluster, the desired cluster is isolated by radiation pressure ejection.

16. The method according to claim 1, wherein the microarray substrate comprises a front surface in direct contact with the clusters and a back surface opposite to the front surface, and wherein the step of selectively isolating the desired cluster applies the energy to the microarray substrate from the back surface.

\* \* \* \* \*